(12) United States Patent
Klitzke et al.

(10) Patent No.: US 12,390,493 B2
(45) Date of Patent: *Aug. 19, 2025

(54) FIBROUS BIRTH TISSUE COMPOSITION AND METHOD OF USE

(71) Applicant: Convatec, Inc, Bridgewater, NJ (US)

(72) Inventors: Kurt Klitzke, Memphis, TN (US); Jon G. Hargis, Memphis, TN (US)

(73) Assignee: CONVATEC, INC, Bridgewater, NJ (US)

( * ) Notice: Subject to any disclaimer, the term of this patent is extended or adjusted under 35 U.S.C. 154(b) by 179 days.

This patent is subject to a terminal disclaimer.

(21) Appl. No.: 18/108,699

(22) Filed: Feb. 13, 2023

(65) Prior Publication Data

US 2023/0190823 A1 Jun. 22, 2023

Related U.S. Application Data

(63) Continuation of application No. 16/284,351, filed on Feb. 25, 2019, now Pat. No. 11,602,548.

(60) Provisional application No. 62/635,093, filed on Feb. 26, 2018.

(51) Int. Cl.

| | |
|---|---|
| *A61K 35/50* | (2015.01) |
| *A61K 35/51* | (2015.01) |
| *A61K 38/39* | (2006.01) |
| *A61K 38/18* | (2006.01) |
| *A61L 27/36* | (2006.01) |

(52) U.S. Cl.
CPC .............. *A61K 35/50* (2013.01); *A61K 35/51* (2013.01); *A61K 38/39* (2013.01); *A61K 38/18* (2013.01); *A61L 27/3608* (2013.01); *A61L 27/362* (2013.01)

(58) Field of Classification Search
None
See application file for complete search history.

(56) References Cited

U.S. PATENT DOCUMENTS

| | | | |
|---|---|---|---|
| 4,647,283 | A | 3/1987 | Carpentier et al. |
| 5,756,678 | A | 5/1998 | Shenoy |
| 6,203,755 | B1 | 3/2001 | Odland |
| 7,795,493 | B2 | 9/2010 | Phelps et al. |
| 8,106,251 | B2 | 1/2012 | Ayares et al. |
| 9,642,937 | B2 | 5/2017 | Zhao et al. |
| 9,808,491 | B2 | 11/2017 | Tseng et al. |
| 11,116,871 | B2 | 9/2021 | Daniel |
| 2002/0160510 | A1 | 10/2002 | Hariri |
| 2004/0048796 | A1 | 3/2004 | Hariri |
| 2007/0038298 | A1 | 2/2007 | Sulner |
| 2013/0230561 | A1 | 9/2013 | Daniel |
| 2015/0182664 | A1 | 7/2015 | Ayares et al. |
| 2015/0250829 | A1 | 9/2015 | Daniel et al. |
| 2018/0126036 | A1 | 5/2018 | Early |

FOREIGN PATENT DOCUMENTS

| | | |
|---|---|---|
| CN | 107007885 A | 8/2018 |
| EP | 0738106 B1 | 8/2001 |
| WO | 2003030949 A1 | 4/2003 |
| WO | 2012141454 A2 | 10/2012 |
| WO | 2015017500 A1 | 2/2015 |
| WO | 2017017474 A1 | 2/2017 |
| WO | 2017076782 A1 | 5/2017 |
| WO | 2017140914 A1 | 8/2018 |

OTHER PUBLICATIONS

Castellanos et al. "Amniotic membrane application for the healing of chronic wounds and ulcers" 2017, Placenta, vol. 59: 146-153. (Year: 2017).*
Brantley JN, Verla TD. Use of Placental Membranes for the Treatment of Chronic Diabetic Foot Ulcers. Adv Wound Care (New Rochelle). Sep. 1, 2015;4(9):545-559. (Year: 2015).
Balestrini JL, Gard AL, Liu A, Leiby KL, Schwan J, Kunkemoeller B, Calle EA, Sivarapatna A, Lin T, Dimitrievska S, Cambpell SG, Niklason LE. Production of decellularized porcine lung scaffolds for use in tissue engineering. Integr Biol (Camb). Dec. 2015;7(12): 1598-610. (Year: 2015).
Gilpin A, Yang Y. Decellularization Strategies for Regenerative Medicine: From Processing Techniques to Applications. Biomed Res Int. 2017;2017:9831534. (Year: 2017).
Deshmukh SN, Dive AM, Moharil R, Munde P. Enigmatic insight into collagen. J Oral Maxillofac Pathol. May-Aug. 2016;20(2):276-83. (Year: 2016).
Kosswig, K. Surfactants. Ullman's Encycl. Ind. Chem. 2012, A25, 450. (Year: 2012).
Furukawa, S. "A comparison of the histological structure of the placenta in experimental animals", J. Toxicol Pathol (2014), vol. 27, pp. 11-18.
Wu et al. "Wound healing effects of porcine placental extracts on rats with thermal injury" (2003), British J Dermatology, vol. 148: 236-245. (Year: 2003).
Leonel et al. "Decellularization of placentas: establishing a protocol" (Jan. 2018), Brazilian J Med Biol Res, 51(1): 1-12 e6382. (Year:2018).
Gupta et al., "Amnion and Chorion Membranes: Potential Stem Cell Reservoir with Wide Applications in Periodontics", 2015, International Journal of Biomaterials, vol. 2015, p. 1-9.
Agilent Technologies, "Safety Data Sheet: Phosphate Buffer Saline—PBS", 2015, https://www.agilent.com/cs/library/msds/SDS211_NAEnglish.pdf, [accessed: Sep. 22, 2020].
Office Action from corresponding U.S. Appl. No. 16/270,052, dated Apr. 1, 2022.

* cited by examiner

Primary Examiner — Teresa E Knight
(74) Attorney, Agent, or Firm — Barnes & Thornburg LLP

(57) ABSTRACT

A fibrous birth tissue composition fabricated from placental tissue is provided. Methods of processing a mammal's placental tissue to form a fibrous birth tissue composition are provided. Regenerative methods are also provided.

8 Claims, No Drawings

FIBROUS BIRTH TISSUE COMPOSITION AND METHOD OF USE

CROSS-REFERENCE TO RELATED APPLICATIONS

The present application is a continuation of U.S. Ser. No. 16/284,351, filed Feb. 25, 2019 which claims priority to U.S. Provisional Application Ser. No. 62/635,093, filed Feb. 26, 2018, the content of which is incorporated herein in its entirety.

BACKGROUND OF THE INVENTION

Human placental tissue has been utilized for various purposes over the past century for regenerative medicine purposes. There remains a need, however, for regenerative products and methods of producing novel human placental tissue products, as well as regenerative products derived from alternative sources.

SUMMARY OF THE INVENTION

The present disclosure is generally directed to fibrous birth tissue compositions, and processes for producing the fibrous birth tissue compositions. The fibrous birth tissue compositions exhibit various regenerative medical properties. The fibrous birth tissue compositions may be placed in or around various wounds of a patient in need. The fibrous birth tissue compositions as provided herein are particularly advantageous in that the fibers self-adhere to one another and to a wound to aid in the healing cascade. The fibrous birth tissue compositions will stay in contact with the wound and not easily migrate or move away from the wound.

According to one aspect, a fibrous birth tissue composition is provided. The composition includes at least one porcine placental tissue in the form of one or more fibers. According to one embodiment, the at least one porcine placental tissue is cut to form one or more fibers. According to one embodiment, the one or more fibers is between from about 1 micrometer to about 100 millimeters in length. According to one embodiment, the one or more fibers is between from about 0.1 micrometer to about 10 millimeters in width. According to one embodiment, the at least one porcine placental tissue is at least one placental membrane, at least one amnion membrane, at least one chorion membrane, at least one intermediate layer, at least one placental globe, at least one umbilical cord, or any combination thereof.

According to another aspect, a fibrous birth tissue composition is provided that includes a mammalian placental tissue treated with a bioburden reduction step, a detergent treatment step, a viral inactivation step, and milled into one or more fibers. According to one embodiment, the mammalian placental tissue exhibits a pH of between about 6.8 and about 7.2. According to one embodiment, the mammalian placental tissue includes a dehydrated porcine placental membrane comprising collagen I, collagen IV, elastin, laminin, fibronectin and hyaluronic acid.

According to one aspect, a bone substitute composition is provided. According to one embodiment, the bone substitute composition includes a fibrous birth tissue composition as provided herein and a bone material. According to one embodiment, the bone material is derived from porcine bone. According to one embodiment, the porcine bone is from an adolescent pig. According to one embodiment, the bone material is in a powdered or ground formulation.

According to one aspect, a method of treating a wound is provided. The method includes the step of placing a fibrous birth tissue composition as provided herein on or around a wound or wound bed. According to one embodiment, the wound or wound bed is a surgical site, ulcer, abrasion, tissue void or burn. According to one embodiment, the fibrous birth tissue composition adheres to the wound. According to one embodiment, the fibrous birth tissue composition absorbs exudate secreted from a wound.

According to one aspect, a kit is provided. The kit includes a fibrous birth tissue composition as provided herein and instructions for use.

According to one aspect, a method of preparing a fibrous birth tissue composition is provided. The method includes the steps of:
a) introducing from about 1 mL to about 40 mL of from about 1M to about 4M sodium chloride solution per gram of placental tissue to the placental tissue;
b) decanting the sodium chloride;
c) rinsing the sodium chloride from the placental tissue with water;
d) introducing from about 5 mL to about 25 mL of a detergent solution per gram of placental tissue to the placental tissue;
e) decanting the detergent solution;
f) rinsing the detergent solution from the placental tissue with water;
g) introducing from about 5 mL to about 15 mL of from about 0.1M to about 1.0M sodium hydroxide per gram of placental tissue to the placental tissue;
h) rinsing the sodium hydroxide from the placental tissue with water;
i) introducing from about 5 mL to about 50 mL of buffer solution per gram of placental tissue to the placental tissue;
j) decanting the buffer solution;
k) measuring the pH of the placental tissue;
l) repeating steps i), j) and k) until the pH of the placental tissue is between about 6.8 and about 7.2;
m) rinsing the buffer solution from the placental tissue with water; and
n) milling the placental tissue into fibers to form a fibrous birth tissue composition. According to one embodiment, the detergent solution includes at least one anionic detergent and at least one protease enzyme. According to one embodiment, the detergent solution includes sodium linear alkylaryl sulfonate, phosphates, carbonates and at least one protease enzyme. According to one embodiment, the female mammal is a pig that is not genetically modified to halt or reduce expression of a functional alpha-1,3 galactosyltransferase gene. According to one embodiment, the method further includes the steps of:
o) packaging the placental tissue; and
p) terminally sterilizing the packaged placental tissue. According to one embodiment, the method of preparing the fibrous birth tissue composition includes the step of dehydrating the placental tissue immediately prior to milling the placental tissue into fibers.

According to another aspect, a fibrous birth tissue composition is provided that is produced by any of the aforementioned methods.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements.

As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

The present disclosure provides a fibrous birth tissue composition that is prepared from mammalian birth tissue. The present disclosure particularly provides a porcine birth tissue composition that is prepared from pig birth tissue.

As used herein, the terms "birth tissue" and "placental tissue" include, but are not limited to, elements of a mammalian placental organ such as, for example, mammalian placental membrane, mammalian amnion, mammalian chorion, mammalian intermediate layer, mammalian placental globe, mammalian umbilical cord, or a combination thereof.

As used herein, the term "placental membrane" refers to the full, intact placental membrane including the amnion and chorion layers that are obtained from a mammal such as, for example, a pig or human.

As used herein, the terms "pig" and "porcine" may be used interchangeably.

As used to herein, the term "birth tissue composition" refers to a construct that is applied onto or around an injured area of a mammalian body.

As used herein, the term "wound" refers to an injured area of the body.

As used herein, the term "fibrous" refers to the form and shape of the birth tissue which includes one or more fibers.

The fibrous birth tissue compositions as provided herein may aid in the healing cascade or healing process of a mammalian wound. In a preferred embodiment, the fibrous birth tissue compositions are fully resorbed by the mammal's body during the healing process. The present disclosure further relates to methods for aseptically processing birth tissue to produce a fibrous birth tissue composition.

The fibrous birth tissue composition includes at least one fiber formed from birth tissue that is processed as provided herein. According to a particular embodiment, the fibrous birth tissue composition includes a plurality of fibers formed from birth tissue that is processed as provided herein.

According to one embodiment, the fibers are of various lengths and widths (i.e., random lengths and widths). According to one embodiment, each fiber is typically from about 1 micrometer to about 100 millimeters in length. According to one embodiment, each fiber is typically from about 100 micrometers to about 10 millimeters in length. According to one embodiment, each fiber is typically from about 0.1 micrometer to about 10 millimeters in width. According to one embodiment, each fiber is typically from about 10 micrometers to about 500 micrometers in width.

According to one embodiment, each fiber as provided herein is self-adhering. Accordingly, each fiber will adhere to one another and conglomerate. Likewise, each fiber may adhere to a target site such as, for example, a wound or wound bed. While not being bound by a particular theory, the fibers are believed to self-adhere due to naturally or environmentally occurring electrostatic discharge. According to one embodiment, each fiber may draw up or absorb any exudate that is secreted from a wound such as a wound bed or surgical site.

The fibrous birth tissue compositions may be used for a variety of regenerative medicine purposes. According to one embodiment, the regenerative medical use is for treatment of wounds. Other suitable uses include inflammation reduction (anti-inflammatory); pain reduction; anti-adhesion; skin wrinkle reduction, skin resurfacing, skin rejuvenation, and other cosmetic purposes; nerve repair; soft tissue repair; bone repair; joint pain treatment; dura preservation; ocular defect treatment and other similar regenerative uses. Exemplary wounds that may be treated with the birth tissue compositions as provided herein include partial and full thickness wounds; pressure ulcers; venous ulcers; diabetic ulcers; chronic vascular ulcers; tunneled/undermined wounds; surgical wounds (e.g., donor sites/grafts, post-Mohs surgery, post-laser surgery, podiatric, wound dehiscence); trauma wounds (e.g., abrasions, lacerations, second degree burns, skin tears); and draining wounds. The fibrous birth tissue compositions may also be utilized on any wound arising on or around a soft tissue, nerve, organ, vascular tissue, muscle, spinal cord, bone, oral cavity, ocular surface, or a combination thereof.

According to one embodiment, the fibrous birth tissue compositions provided herein may be treated to provide for the delivery of a variety of antibiotics, anti-inflammatory agents, growth factors and/or other specialized proteins or small molecules. The fibrous birth tissue compositions may include any one or more of a variety of mammalian placental tissue such as, for example, mammalian placental membrane, mammalian amnion, mammalian chorion, mammalian placental globe, mammalian umbilical cord or a combination thereof. The fibrous birth tissue composition may include any variety of porcine birth tissue such as, for example, porcine placental membrane, porcine amnion, porcine chorion, porcine placental globe, porcine umbilical cord or a combination thereof.

According to one embodiment, a method of preparing a fibrous birth tissue composition is provided. The method includes the step of collecting the placental tissue from a female mammal. According to one embodiment, the method includes the step of collecting the placental tissue from a female pig. According to one embodiment, the female pig is not genetically modified to halt or reduce expression of the functional alpha-1,3 galactosyltransferase gene. According to one embodiment, the placental tissue collected is the placental membrane with the umbilical cord attached. Potential placental tissue donors are screened and tested to exclude any donors that may present a health risk. According to one embodiment, placental tissue is recovered from a full-term delivery of one or more offspring such as an infant or piglet(s). According to one embodiment, the method further includes the step of placing the placental tissue in a transport container. According to one embodiment, the method further includes the step of placing the placental tissue in a transport container containing a transport solution.

According to one embodiment, the method further includes the step of rinsing the placental tissue with water. According to a particular embodiment, the water is sterile water. According to a particular embodiment, the water is type 1 water. According to one embodiment, the method further includes the step of removing a substantial portion of any residual moisture present on the placental tissue.

According to one embodiment, the method further includes the step of freezing the umbilical cord and placental tissue. According to one embodiment, the placental tissue may be kept frozen until further processing is needed. According to one embodiment, the method further includes the step of removing the frozen, bagged placental tissue from the freezer and thawing in a refrigerator for about three (3) to five (5) days. According to one embodiment, the method further includes the step of thawing the placental tissue at ambient temperature.

According to one embodiment, the method includes rinsing the placental tissue with water. According to a particular embodiment, the water is sterile water. According to one embodiment, the water is type 1 water. According to one embodiment, the method includes draining the placental tissue. According to one embodiment, the method includes the step of opening any tube-shaped placental tissue so the placental tissue will lie flat onto a cutting surface. According to one embodiment, the method includes separating the placental membrane from the umbilical cord.

According to one embodiment, the method includes the step of dividing the placental tissue into pieces. According to one embodiment, a rotary cutter or other suitable cutter is used to cut the pieces.

According to one embodiment, the method optionally includes the step of removing Wharton's jelly and excess fluids from the placental tissue to produce cleaned placental tissue. According to one embodiment, the method includes the step of weighing the cleaned placental tissue on a tared balance.

According to one embodiment, the method includes the step of treating the placental tissue with a bioburden reduction solution. According to a one embodiment, the bioburden reduction solution is sodium chloride. According to one embodiment, the method includes the step of adding from about 1 mL to about 40 mL of from about 1M to about 4M sodium chloride solution per gram of placental tissue to the cleaned placental tissue. According to one embodiment, the method includes the step of adding from about 5 mL to about 25 mL of 3M sodium chloride solution per gram of placental tissue to the cleaned placental tissue. According to one embodiment, the method includes the step of adding about 20 mL of 3M sodium chloride solution per gram of placental tissue to the cleaned placental tissue.

According to one embodiment, the method includes the step of immersing the placental tissue in the sodium chloride solution from about thirty minutes to about two hours. According to a preferred embodiment, the method includes the step of immersing the placental tissue in the sodium chloride solution for about one hour. According to one embodiment, the method includes the step of shaking the placental tissue in the sodium chloride solution from about thirty minutes to about two hours at about 50 RPM to about 100 RPM. According to a preferred embodiment, the method includes the step of shaking the placental tissue in the sodium chloride solution for about one hour at about 50 RPM to about 100 RPM. According to one embodiment, the placental tissue is shaken on an orbital shaker table.

According to one embodiment, the method includes the step of decanting the sodium chloride. According to one embodiment, the method includes the step of rinsing the placental tissue with water. According to a particular embodiment, the water is sterile water. According to one embodiment, the water is type 1 water. According to one embodiment, the method includes the step of rinsing the placental membrane with from about 5 mL to about 25 mL of water per gram of placental tissue. According to a particular embodiment, the method includes the step of rinsing the placental tissue with about 20 mL of water per gram of placental tissue. According to one embodiment, the placental tissue is rinsed one time. According to one embodiment, the placental tissue is rinsed at least two times. According to one embodiment, the placental tissue is rinsed at least three times. According to one embodiment, the method includes the step of removing excess fluids from the placental tissue.

According to one embodiment, the method includes the step of placing the placental tissue in from about 5 mL to about 25 mL of a detergent solution. According to a particular embodiment, the method includes the step of placing the placental tissue in about 20 mL of a detergent solution. According to a particular embodiment, the method includes the step of placing the placental tissue in about 20 mL of a detergent solution per gram of placental tissue. According to one embodiment, the detergent is present at a concentration of about 0.25% to about 3% w/v. According to one embodiment, the detergent is present at a concentration of about 1% w/v. According to a particular embodiment, the detergent solution includes at least one anionic detergent and at least one protease enzyme. According to one embodiment, the detergent solution includes sodium linear alkylaryl sulfonate, phosphates, carbonates and at least one protease enzyme. According to one embodiment, the detergent solution is commercially available under the trade name Tergazyme™. According to one embodiment, the detergent solution is a 1% Tergazyme™ solution.

According to one embodiment, the method includes the step of immersing the placental tissue in the detergent solution for from about one hour to about three hours. According to a particular embodiment, the method includes the step of immersing the placental tissue in the detergent solution for about two hours. According to one embodiment, the method includes the step of shaking the placental tissue in the detergent solution for from about one hour to about three hours at about 50 RPM to about 100 RPM. According to one embodiment, the method includes the step of shaking the placental tissue in the detergent solution for about two hours at about 50 RPM to about 100 RPM. According to one embodiment, the placental tissue is shaken on an orbital shaker table.

According to one embodiment, the method includes the step of decanting the detergent solution. According to one embodiment, the method includes the step of rinsing the placental tissue with from about 5 mL to about 25 ml of water per gram of placental tissue. According to one embodiment, the method includes the step of rinsing the placental tissue with about 20 ml of water per gram of placental tissue. According to a particular embodiment, the water is sterile water. According to one embodiment, the water is type 1 water. According to one embodiment, the placental tissue is rinsed one time. According to one embodiment, the placental tissue is rinsed at least two times. According to one embodiment, the placental tissue is rinsed at least three times. According to one embodiment, the method includes the step of removing excess fluids from the placental tissue.

According to one embodiment, the method includes the step of treating the placental tissue with a viral inactivation solution. According to a one embodiment, the viral inactivation solution is sodium hydroxide. According to one embodiment, the method includes the step of adding or introducing from about 5 mL to about 15 mL of about from about 0.1M to about 1.0M sodium hydroxide per gram of placental tissue. According to one embodiment, the method includes the step of adding or introducing from about 5 mL to about 15 mL of 0.25M sodium hydroxide per gram of placental tissue. According to one embodiment, the method includes the step of adding or introducing about 10 mL of 0.25M sodium hydroxide per gram of placental tissue.

According to one embodiment, the method includes the step of immersing the placental tissue in the sodium hydroxide for about 15 minutes to about 45 minutes. According to one embodiment, the method includes the step of immersing the placental tissue in the sodium hydroxide for about 20 minutes. According to one embodiment, the method includes the step of shaking the placental tissue in the sodium hydroxide for about 15 minutes to about 45 minutes at about 50 RPM to about 100 RMP. According to one embodiment, the method includes the step of shaking the placental tissue in the sodium hydroxide for about 20 minutes at about 50 RPM to about 100 RPM. According to one embodiment, the placental tissue is shaken on an orbital shaker table. The sodium hydroxide may then be decanted. According to one embodiment, the steps of adding sodium hydroxide, shaking and decanting may be repeated as many times as necessary to inactivate any viruses present in the placental tissue to produce a placental tissue that is substantially void of viruses. According to one embodiment, the steps of adding sodium hydroxide, shaking and decanting may be repeated once. According to one embodiment, the steps of adding sodium hydroxide, shaking and decanting may be repeated twice.

According to one embodiment, the method includes the step of rinsing the placental tissue with water. According to a particular embodiment, the water is sterile water. According to one embodiment, the water is type 1 water. According to a particular embodiment, the step of rinsing the placental tissue with sterile water is carried out for up to about 10 minutes. According to one embodiment, the method includes the step of removing excess fluids from the placental tissue.

According to one embodiment, the method includes the step of adding or introducing from about 5 mL to about 50 mL of buffer solution per gram of placental tissue. According to a particular embodiment, the method includes the step of adding or introducing about 20 ml of buffer solution per gram of placental tissue. According to one embodiment, the method includes the step of immersing the placental tissue in the buffer solution. According to one embodiment, the method includes the step of shaking the placental tissue in the buffer solution for about 5 minutes to about 45 minutes at about 50 RPM to about 100 RPM. According to one embodiment, the method includes the step of shaking the placental tissue in the buffer solution for about 20 minutes at about 50 RPM to about 100 RPM. According to one embodiment, the placental tissue is shaken on an orbital shaker table. The buffer solution may then be decanted.

According to a one embodiment, the buffer solution is phosphate-buffered saline. According to one embodiment, the method includes the step of measuring the pH of the placental tissue after buffer solution treatment. According to one embodiment, the steps of adding buffer solution, shaking and decanting may be repeated until the pH of the placental tissue is between about 6.8 and about 7.2.

According to one embodiment, the method includes the step of rinsing the placental tissue with water. According to a particular embodiment, the water is sterile water. According to one embodiment, the water is type 1 water. According to one embodiment, the placental tissue is rinsed one time. According to one embodiment, the rinsing step is carried out multiple times. According to a one embodiment, the rinsing step is carried out at least twice. According to a one embodiment, the rinsing step is carried out at least three times. According to one embodiment, the method further includes the step of removing a substantial portion of any residual moisture present in the placental tissue.

When preparing a fibrous birth tissue composition, the method optionally includes the step of dehydrating the placental tissue. According to one embodiment, the placental tissue may be dehydrated by any method known in the art, including, but not limited to, chemical dehydration (e.g., organic solvents), lyophilization, desiccation, oven dehydration and air drying. According to a preferred embodiment, the method includes the step of adding or introducing an alcohol to the placental tissue to cover the entire surface of the placental tissue (i.e., submerge the placental tissue). According to one embodiment, the method includes the step of adding or introducing from about 1 mL to about 10 mL of alcohol per gram of placental tissue. According to one embodiment, the method includes the step of adding or introducing about 5 mL of alcohol per gram of placental tissue. According to one embodiment, the placental tissue is fully submerged in the alcohol for from about one hour to about 24 hours. According to one embodiment, the placental tissue is not agitated while in contact with the alcohol. The alcohol may be any alcohol which is safe and appropriate for contact with placental tissue. According to a particular embodiment, the alcohol is ethanol. According to another embodiment, the ethanol is from about 90%-100% ethanol. According to a particular embodiment, the ethanol is 200 proof (i.e., absolute ethanol). According to one embodiment, the method includes the step of decanting or draining the alcohol from the placental tissue.

According to one embodiment, the optional dehydration method may be carried out by spreading the placental tissue onto a drying table. According to one embodiment, the placental tissue may be blotted with a micro fiber wipe or similar. The placental tissue may be spread in a manner so as to fully dehydrate the placental tissue while ensuring no wrinkles or bubbles are present.

According to one embodiment, the optional dehydration method may be carried out by lyophilizing the placental tissue. According to a particular embodiment, the method includes the steps of placing the placental tissue on a lyophilization tray and spreading the placental tissue out evenly. The tray containing the placental tissue may then be subject to a lyophilization drying cycle to produce a dehydrated placental tissue. The dehydrated placental tissue may be stored until further processing is required.

According to one embodiment, the method includes the step of cutting the placental tissue into a plurality of strips. According to one embodiment, the strips of placental tissue may be milled into one or more fibers. The fibers may be produced using milling/grinding instruments known in the art, including, but not limited to, oscillating mills, cryogenic mills, dispersers, and homogenizers. According to one embodiment, the milling step is carried out by running the placental tissue through an analytical mill at least once. According to one embodiment, the milling step is carried out by running the placental tissue through an analytical mill at least twice. According to one embodiment, the analytical mill is equipped with a screen to ensure output is of the desired fiber size. According to one embodiment, the milled placental tissue may be passed through a series of sieves to ensure desired fiber size. According to another embodiment, placental tissue may be reduced to fibers through hydrolyzation or solubilization followed by lyophilization and milling. According to one embodiment, multiple or serial milling steps/methods and multiple or serial size screening steps/methods may be utilized to render placental tissue to fibers within the following categories: (i) nano fibrils: 300 nanometers to 1000 nanometers; (ii) micro fibrils: 1 micrometer to 1000 micrometers; and (iii) macro fibrils: 1 millimeter to 10 millimeters.

According to one embodiment, the fibrous birth tissue composition as provided herein may be placed in a proper package. A suitable package includes a vial or a pouch. According to one embodiment, the chosen package may then be placed into and sealed within an outer package.

According to one embodiment, the method includes the step of terminally sterilizing the packaged fibrous birth tissue composition. According to one embodiment, the method of terminal sterilization may be e-beam irradiation, gamma irradiation, peracetic acid treatment, vaporized peracetic acid (VPA) treatment, any combination thereof, or any other terminal sterilization method known in the art.

The fibrous birth tissue composition as provided herein may be combined with a bone material or bone substitute material. According to one embodiment, the fibrous birth tissue composition as provided herein may be combined with one or more of cancellous bone, demineralized cancellous bone, allograft (fresh or fresh-frozen), freeze dried bone allograft, demineralized freeze dried bone allograft, cortical cancellous bone, or a combination thereof. According to one embodiment, the fibrous birth tissue composition as provided herein may be combined with an osteoinductive or osteoconductive bone material. According to a particular embodiment, the fibrous birth tissue composition as provided herein may be combined with demineralized bone or demineralized bone matrix. According to a particular embodiment, the bone material as provided herein is derived from porcine bone. According to one embodiment, the porcine bone is derived from a young or adolescent pig which typically exhibits a higher content of bone morphogenetic protein 2 (BMP-2) compared to an adult pig, bovine or human source. According to one embodiment, porcine bone is treated with hydrochloric acid and ground to form pieces, chips or a powder.

According to one embodiment, the dehydrated porcine placental membranes utilized in the fibrous birth tissue composition as provided herein include one or more of collagen I, collagen IV, elastin, laminin, fibronectin and hyaluronic acid. According to one embodiment, each of the one or more of collagen I, collagen IV, elastin, laminin, fibronectin and hyaluronic acid is present in the dehydrated porcine placental membrane in an amount that is different from a porcine placental membrane that is not processed according to one or more of the processing steps provided herein. According to one embodiment, collagen I is present in an amount of from about 0.001% w/w to about 99.9% w/w based on the total weight of the placental membrane. According to one embodiment, collagen IV is present in an amount of from about 0.001% w/w to about 99.9% w/w based on the total weight of the placental membrane. According to one embodiment, elastin is present in an amount of from about 0.001% w/w to about 99.9% w/w based on the total weight of the placental membrane. According to one embodiment, laminin is present in an amount of from about 0.001% w/w to about 99.9% w/w based on the total weight of the placental membrane. According to one embodiment, fibronectin is present in an amount of from about 0.001% w/w to about 99.9% w/w based on the total weight of the placental membrane. According to one embodiment, hyaluronic acid is present in an amount of from about 0.001% w/w to about 99.9% w/w based on the total weight of the placental membrane.

A method of treating a wound is also provided. According to one embodiment, the method includes the step of providing a fibrous birth tissue composition as provided herein. According to one embodiment, the method includes the step of placing the fibrous birth tissue composition on or around a wound. According to one embodiment, the birth tissue composition is introduced directly in the wound bed or around the wound. According to one embodiment, the birth tissue composition is introduced to pack a wound. The wound may be a burn, cut, abrasion, tissue void or ulcer. According to one embodiment, the ulcer is a tunneling diabetic foot ulcer. According to such an embodiment, the fibrous birth tissue composition may function as a topical overlay application.

According to one embodiment, a method of treating a tissue void is provided. According to one embodiment, the method includes the step of filling the tissue void with the fibrous birth tissue composition. According to one embodiment, the void may be found anywhere in or on the mammalian body including, for example, an oral void created by oral surgery or tooth extraction or a bone void.

According to one embodiment, a method of treating a surgical site is provided. According to one embodiment, the method includes the step of applying the fibrous birth tissue composition to a surgical site anywhere on a mammalian body.

According to one embodiment, a method of covering an implant or other device that may be placed on or within a mammalian body is provided. According to one embodiment, the method includes the step of applying the fibrous birth tissue composition on or around the implant.

A kit is also provided. The kit includes a fibrous birth tissue composition as provided herein. The kit may also include instructions for use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

EXAMPLE

Porcine placental membrane was processed according to the methods as provided herein. Particularly, porcine placental membrane was treated with a bioburden solution, treated with a detergent solution, treated with a viral inactivation solution and dehydrated according the methods as provided herein. The resulting dehydrated porcine placental membrane was analyzed to assess the presence of the following extracellular matrix components: collagen I, collagen IV, elastin, laminin, fibronectin, and hyaluronic acid (HA). An immunostaining procedure was carried out utilizing a primary antibody to detect the specific protein in the sample and then a secondary antibody was labeled with a fluorophore to detect any bound primary antibody. Utilizing this methodology enabled improved detection of the primary antibodies since two or more secondary antibodies can detect a single primary antibody and thereby increase the fluorescent signal for imaging.

The following primary antibodies were used:
Rabbit Anti-Collagen I antibody (Cat #ab34710 Abcam, Cambridge, MA, USA).
Rabbit Anti-Collagen IV antibody (Cat #ab6586 Abcam, Cambridge, MA, USA).
Rabbit Anti-Elastin antibody (Cat #ab21610 Abcam, Cambridge, MA, USA)
Rabbit Anti-Laminin antibody (Cat #ab11575 Abcam, Cambridge, MA, USA).
Rabbit Anti-Fibronectin antibody (Cat #ab2413 Abcam, Cambridge, MA, USA).
Mouse Anti-Hyaluronic Acid antibody (Cat #CAU29210 Biomatik, Wilimgton, DE, USA)
The following secondary antibodies were used:
Anti-Rabbit 488 secondary antibody (provided by the Integrated Microscopy Center, The University of Memphis, Memphis, TN, USA).
Anti-Mouse 594 secondary antibody (provided by the Integrated Microscopy Center, The University of Memphis, Memphis, TN, USA).

One centimeter diameter samples were cut at random from ten sterile porcine placental membrane samples (approximately 2.5 cm diameter by <0.5 mm thick). Triplicate samples were evaluated for each matrix component. Samples were attached to cover slips (approximately 2 cm diameter) using phosphate buffered saline (PBS). The samples were allowed to dry at ambient conditions overnight. Samples were then were soaked in 1% NP-40 (a detergent used to increase permeability of biological specimen for staining procedures) for 5 minutes and then rinsed three times with approximately 1 ml of PBS. The primary antibodies for collagen I, collagen IV, elastin, laminin, fibronectin, and hyaluronic acid (HA) were diluted 1:20 in PBS. The samples were covered with 50 µl of the primary antibody dilutions and incubated overnight at 4° C. The next day, the samples were rinsed three times with approximately 1 ml PBS to remove unbound primary antibodies. The secondary antibodies were diluted 1:50 in PBS and the samples were covered with 50 µl of the secondary antibodies. The anti-rabbit 488 secondary antibody was used for the collagen I, collagen IV, elastin, fibronectin, and laminin samples. The anti-mouse 594 secondary antibody was used for the hyaluronic acid (HA) sample. After 1 hour of incubation at 4° C., the samples were again rinsed three times with 1 ml PBS to remove unbound secondary antibodies. The coverslips were mounted to slides (7.5 cm long×2.5 cm wide) using Slowfade Diamond Antifade Mountant (Fisher Scientific). Slides were examined using a confocal laser scanning microscope (Ti-E A1rSi System, Nikon Instruments, Inc. Melville, NY, USA) at 20× magnification. Secondary only controls (sections stained only with the secondary antibodies) were used to adjust brightness and intensity to account for any background fluorescence due to non-specific antibody absorption on to samples. Brightness and intensity settings were kept uniform so that images from all groups could be compared. Samples were imaged using optical sectioning. For the optical sectioning, between 35-55 slices or planes of focus were collected starting at the surface and moving into the sample at approximately 0.51 µm intervals. The collected images were stacked to create a composite image. There were n=3 images collected for each extracellular matrix component evaluated.

The sterilized porcine placental membranes showed positive staining for each of collagen I, collagen IV, elastin, laminin, fibronectin, and hyaluronic acid (HA). Collagen I and collagen IV showed the highest intensity of staining, although all antibodies did show positive staining. Based on the immunostaining, the porcine placental membranes processed according to the methods as provided herein contained collagen I, collagen IV, elastin, laminin, fibronectin, and hyaluronic acid (HA).

We claim:

1. A method of treating a wound comprising the steps of:
    placing a fibrous birth tissue composition on or around a wound or wound bed, the fibrous birth tissue composition comprising:
        at least one porcine placental membrane treated with a bioburden reduction step, a detergent treatment step, and a viral inactivation step, followed by dehydrating the porcine placental membrane, subsequently cutting or milling the dehydrated porcine placental membrane into one or more fibers, and passing the one or more fibers through a sieve to isolate macro fibrils that form the fibrous porcine birth tissue composition.

2. The method of claim 1, wherein the wound or wound bed is a surgical site, ulcer, abrasion, tissue void or burn.

3. The method of claim 2, wherein the ulcer is a pressure ulcer, venous ulcer, diabetic ulcer, or chronic vascular ulcer.

4. The method of claim 3, wherein the diabetic ulcer is a tunneling diabetic ulcer.

5. The method of claim 1, wherein the fibrous birth tissue composition adheres to the wound.

6. The method of claim 1, wherein the fibrous birth tissue composition absorbs exudate secreted from a wound.

7. The method of claim 1, wherein the detergent includes at least one anionic detergent and at least one protease enzyme.

8. The method of claim 1, wherein the wound is a tunneled/undermined wound, laceration, skin tear, or draining wound.

* * * * *